US008019436B2

(12) United States Patent
Dadd et al.

(10) Patent No.: US 8,019,436 B2
(45) Date of Patent: Sep. 13, 2011

(54) ELECTRODE ASSEMBLY FOR A STIMULATING MEDICAL DEVICE

(75) Inventors: Fysh Dadd, Lane Cove (AU); Dusan Milojevic, Westleigh (AU)

(73) Assignee: Cochlear Limited, Macquarie University, NSW ( * ) Notice: Subject to any disclaimer, the term of this patent is extended or adjusted under 35 U.S.C. 154(b) by 743 days.

(21) Appl. No.: 11/630,643

(22) PCT Filed: Jun. 27, 2005

(86) PCT No.: PCT/AU2005/000915
§ 371 (c)(1),
(2), (4) Date: May 27, 2008

(87) PCT Pub. No.: WO2006/000031
PCT Pub. Date: Jan. 5, 2006

(65) Prior Publication Data
US 2009/0043358 A1    Feb. 12, 2009

(30) Foreign Application Priority Data

Jun. 25, 2004 (AU) ................ 2004903484

(51) Int. Cl.
*A61N 1/00* (2006.01)
(52) U.S. Cl. ........................................... 607/115
(58) Field of Classification Search ............ 204/415; 429/161; 600/373, 374, 126, 137, 152, 115
See application file for complete search history.

(56) References Cited

U.S. PATENT DOCUMENTS

| 4,819,647 | A |   | 4/1989  | Byers et al.    |         |
|-----------|---|---|---------|-----------------|---------|
| 5,266,180 | A | * | 11/1993 | Harnoncourt et al. | 204/415 |
| 6,416,900 | B1| * | 7/2002  | Taenaka et al.  | 429/161 |
| 6,862,805 | B1| * | 3/2005  | Kuzma et al.    | 29/858  |

FOREIGN PATENT DOCUMENTS

| EP | 1013303 B1       | 3/2002  |
|----|------------------|---------|
| WO | WO 02/089907 A1  | 11/2002 |

OTHER PUBLICATIONS

Written Opinion for International Patent Application No. PCT/AU2005/000915, dated Sep. 8, 2005, 6 pages.
International Search Report for International Patent Application No. PCT/AU2005/000915, dated Sep. 9, 2005, 4 pages.
International Preliminary Report on Patentability for International Patent Application No. PCT/AU2005/000915, dated Dec. 28, 2006, 7 pages.

* cited by examiner

*Primary Examiner* — George Manuel
*Assistant Examiner* — Robert N Wieland
(74) *Attorney, Agent, or Firm* — Kilpatrick Townsend & Stockton LLP

(57) ABSTRACT

An implantable electrode assembly for a stimulating medical device, the electrode assembly comprising: an elongate carrier member; one or more electrodes disposed on said carrier member; and one or more signal pathways each extending for a length through at least a part of said carrier member to deliver signals to an associated one of said one or more electrodes, wherein at least one of said one or more signal pathways has a non-uniform cross-sectional profile over a length of said elongate carrier member.

42 Claims, 8 Drawing Sheets

ELECTRODE ASSEMBLY FOR A STIMULATING MEDICAL DEVICE

CROSS-REFERENCE TO RELATED APPLICATIONS

This application is a national stage application under 35 USC §371(c) of PCT Application No. PCT/AU2005/000915, entitled "Electrode Assembly," filed on Jun. 27, 2005, which claims priority from Australian Patent No. 2004903484, filed on Jun. 25, 2004. The entire disclosure and contents of the above applications are hereby incorporated by reference herein.

BACKGROUND

1. Field of the Invention

The present invention relates generally to stimulating medical devices, and more particularly, to an implantable electrode assembly for a stimulating medical device.

2. Related Art

Hearing loss is generally of two types, namely conductive and sensorineural. The treatment of both of types of hearing loss has been quite different, relying on different principles to deliver sound signals to be perceived by the brain as sound. Conductive hearing loss occurs when the normal mechanical pathways for sound to reach the hair cells in the cochlea are impeded, for example, by damage to the ossicles. In such cases, hearing loss is often improved with the use of conventional hearing aids, which amplify the sound so that acoustic information reaches the cochlear hair cells. Such hearing aids utilize acoustic mechanical stimulation, whereby the sound is amplified according to a number of varying techniques, and delivered to the inner ear as mechanical energy. This may be through a column of air to the eardrum, or through direct delivery to the ossicles of the middle ear.

On the other hand, sensorineural hearing loss is due to the absence or destruction of the cochlear hair cells which are needed to transduce acoustic signals into auditory nerve impulses. Individuals suffering from this type of hearing loss are unable to derive any benefit from conventional hearing aid systems regardless of the volume of the acoustic stimulus. This is because the natural mechanisms for transducing sound energy into auditory nerve impulses are either absent or damaged. In such cases, Cochlear™ implants (also referred to as Cochlear™ devices, Cochlear™ prostheses, Cochlear™ implant systems, and the like; simply "cochlear implants" herein) have been developed to provide the sensation of hearing to such individuals. In cochlear implants, electrical stimulation is provided via stimulating electrodes positioned as close as possible to the nerve endings of the auditory nerve, essentially bypassing the hair cells in a normally functioning cochlea. The application of a stimulation pattern to the nerve endings causes impulses to be sent to the brain via the auditory nerve, resulting in the brain perceiving the impulses as sound.

The electrode assembly is inserted during an operation that usually takes between 2-3 hours depending on the device to be implanted. An incision is made behind the ear to expose the temporal bone; the temporal bone consists of the squamous, the mastoid, the tympanic, zygomatic and petrous segment. Typically, cochlear implants require the opening of the mastoid bone which leads to the middle ear. A shallow recess is then created to hold the implant package in place substantially level with the bone. Next a hole is drilled which allows the surgeon access into the cochlea. This hole, referred to as a cochleostomy, extends from the middle ear to the perilymphatic canals of the cochlea. A cochleostomy is typically formed through the round window, the oval window, the promontory or through the apical turn of the cochlea. The electrode assembly is then gently threaded into the shell-like structure of the cochlea and the incision closed; the cochleostomy remains open and heals with scar tissue over the next few days.

In the carrier member, separately insulated, biocompatible conductive wires (e.g., platinum or platinum/iridium) normally extend from the implanted stimulator unit to the electrodes positioned within the cochlea. Signals received by the implantable components are applied by the electrodes leading to stimulation of the auditory nerve. When implanted, the carrier member is potentially exposed to regular mechanical regular movement over time, such as chewing and talking, eventually leading to failure.

SUMMARY

In one aspect of the invention, an implantable electrode assembly for a stimulating medical device is disclosed, the electrode assembly comprising: an elongate carrier member; one or more electrodes disposed on said carrier member; and one or more signal pathways each extending for a length through at least a part of said carrier member to deliver signals to an associated one of said one or more electrodes, wherein at least one of said one or more signal pathways has a non-uniform cross-sectional profile over a length of said elongate carrier member.

In another aspect of the invention, a prosthetic hearing device comprising: an implantable electrode assembly for a stimulating medical device comprising: an elongate carrier member; one or more electrodes disposed on said carrier member; and one or more signal pathways each extending for a length through at least a part of said carrier member to deliver signals to an associated one of said one or more electrodes, wherein at least one of said one or more signal pathways has a non-uniform cross-sectional profile over a length of said elongate carrier member.

BRIEF DESCRIPTION OF THE DRAWINGS

Embodiments of the present invention are described herein with reference to the accompanying drawings, in which.

DETAILED DESCRIPTION

Embodiments of the present invention are described below in connection with one type of stimulating medical device having an implantable electrode assembly, namely a cochlear implant. Cochlear implants use direct electrical stimulation of auditory nerve cells to bypass absent or defective hair cells that normally transduce acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, the cochlear implant provides stimulation of the cochlear nucleus in the brainstem. Such devices, therefore, are commonly referred to as auditory brainstem implants (ABIs).

Exemplary embodiments of a cochlear implant include a Contour™, Freedom™, Nucleus™ or Cochlear™ implant sold by Cochlear Limited, Australia. Such devices are described in U.S. Pat. Nos. 4,532,930, 6,537,200, 6,565,503, 6,575,894, and 6,697,674, the entire contents and disclosures of which are hereby incorporated by reference herein. It should be understood to those of ordinary skill in the art that embodiments of the present invention may be used in other stimulating medical devices such as neurostimulators, cardiac pacemakers/defibrillators, etc. as well as other medical devices which utilize an elongate carrier member to temporarily or permanently implant, deliver or otherwise introduce a therapeutic agent, sensor, device, etc. into a recipient.

Figure 1:
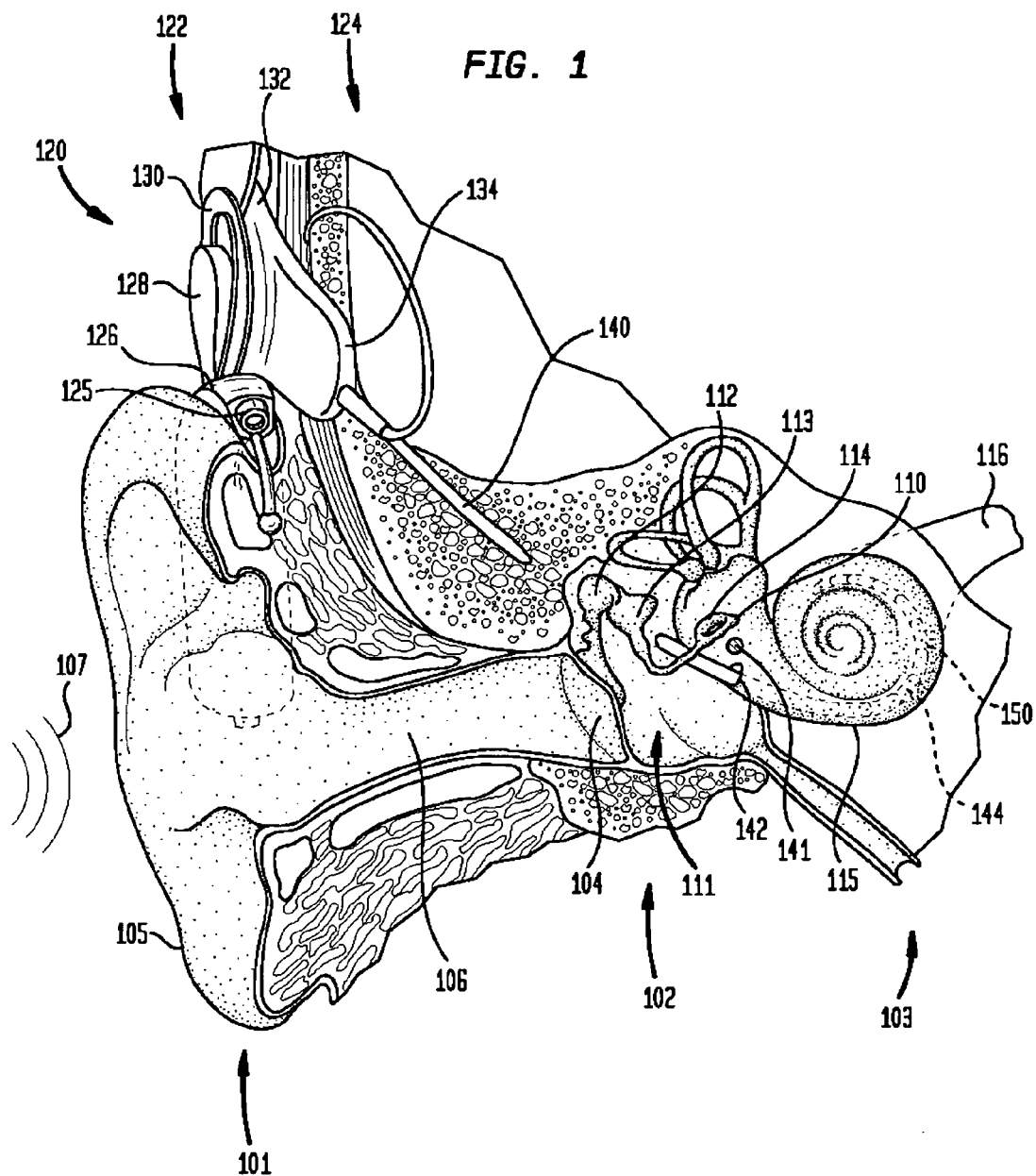
FIG. 1 is a perspective view of one exemplary stimulating medical device, a cochlear implant, in which embodiments of the present invention may be advantageously implemented.

FIG. 1 is a cut-away view of the relevant components of outer ear 101, middle ear 102 and inner ear 103, which are described next below. In a fully functional ear, outer ear 101 comprises an auricle 105 and an ear canal 106. An acoustic pressure or sound wave 107 is collected by auricle 105 and channeled into and through ear canal 106. Disposed across the distal end of ear cannel 106 is a tympanic membrane 104 which vibrates in response to acoustic wave 107. This vibration is coupled to oval window, or fenestra ovalis, 110 through three bones of middle ear 102, collectively referred to as the ossicles 111.

Ossicles 111 comprises the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells (not shown) to auditory nerve 116 and, ultimately, to the brain where they are perceived as sound. In some persons experiencing sensorineural hearing loss, there is an absence or destruction of the hair cells. Cochlear implant 120 is utilized to directly stimulate the ganglion cells to provide a hearing sensation to such persons.

FIG. 1 also shows how cochlear implant 120 is positioned in relation to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is provided to a behind-the-ear (BTE) speech processing unit 126 that generates coded signals. The coded signals are provided to an external transmitter unit 128, along with power from a power source (not shown) such as a battery. External transmitter unit 128 comprises an external coil 130 and, preferably, a magnet (not shown) secured directly or indirectly in external coil 130.

Internal component assembly 124 comprises an internal receiver unit 132 having an internal coil (not shown) that transcutaneously receives power and coded signals from external assembly 122, and provides such signals to a stimulator unit 134. In response to the coded signals, stimulator 134 applies stimulation signals to cochlea 115 via an implanted electrode assembly 140. Electrode assembly 140 enters cochlea 115 via a cochleostomy 142, and has an array 144 of one or more electrodes 150 positioned to be substantially aligned with portions of tonotopically-mapped cochlea 115. The delivery of stimulation signals at various locations along cochlea 115 causes a hearing percept representative of the received sound 107.

While cochlear implant 120 is described as having external components, in another embodiment, the controller, including the microphone, speech processor and power supply, may also be implantable. In such embodiments, the controller may be contained within a hermetically sealed housing or the housing used for stimulator unit 134.

Electrode assembly 140 preferably assumes an optimal electrode position in cochlea 115 upon or immediately following implantation into the cochlea. It is also desirable that electrode assembly 140 be configured such that the insertion process causes minimal trauma to the sensitive structures of cochlea 115. Usually electrode assembly 140 is pre-curved, held in a straight configuration at least during the initial stages of the implantation procedure, conforming to the natural shape of the cochlea during and subsequent to implantation.

Figure 2:
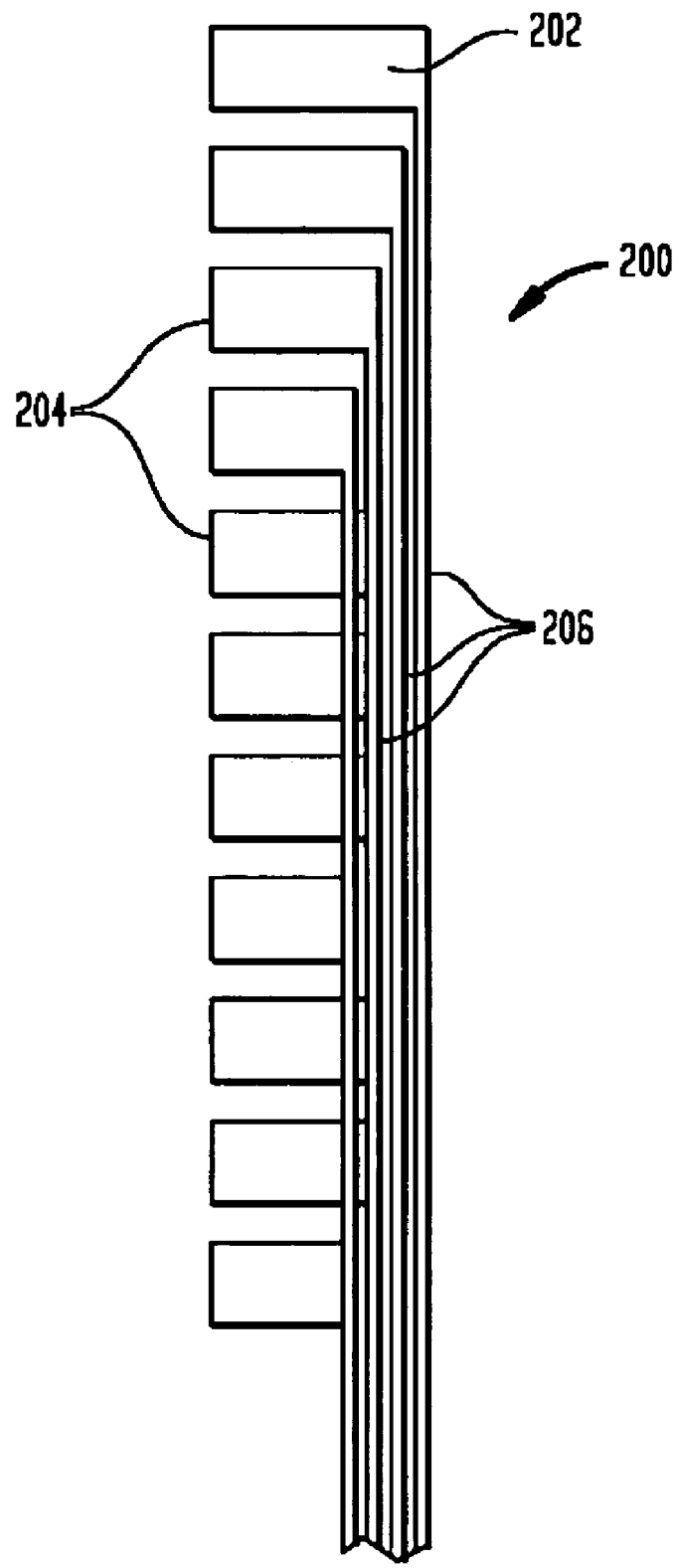
FIG. 2 is a plan view of an electrode assembly in accordance with one embodiment of the present invention.

An embodiment of electrode assembly electrodes 150 and leads (not shown in FIG. 1) that may be formed in part from a worked sheet of, for example, platinum, is depicted generally as 200 in FIG. 2. In FIG. 2, the embodiment of electrodes 150, referred to as electrodes 202, comprise an electrode pad 204 and an integral conductive pathway, lead, filament, or wire 206 extending therefrom. In this exemplary arrangement, conductive pathways 206 are substantially parallel over their length.

The working of the sheet may comprise punching, slicing and/or cutting portions out of a sheet of electrically conducting material. The sheet may also be worked by a process using electrical discharge machining (EDM) as described in the present applicant's International Publication No WO 02/089907, which is hereby incorporated by reference herein. Alternatively, the sheet, or portions of it, may also be eroded by electrochemical means, such as electro-dissolution.

Arrangement 200 is disposed on an electrode carrier member such as carrier member 140 introduced above with reference to FIG. 1. In such embodiments, the intracochlear portion of electrode assembly 140 comprises a carrier member that supports electrodes 202 including pads 204 and wiring 206 that extends from electrode pads 204 back to stimulator unit 134 (FIG. 1). To form an array 144 of electrodes 202, electrode pads 204 and conductive pathways/wires 206 are encapsulated within, for example, a silicone body forming the carrier member. In an alternative embodiment, the carrier member is formed of Silastic MDX 4-4210 is one example of one suitable silicone.

In certain embodiments, conductive pathways 206 decrease in cross-sectional thickness over a portion of their length. For example, in one particular embodiment, the thickness can decrease from between about 10-50 microns to about 1-2 microns. In another embodiment, the thickness of conductive pathways 206 decreases from about 25-50 microns to about 5-25 microns. As one of ordinary skill in the art will appreciate, other dimensions and rate of change of dimensions may be implemented in alternative embodiments, and that selection of such thickness depends are a number of factors. Such factors include, but are not limited to, the anticipated current flow through the conductive pathways, the size of the electrode carrier member, the anticipated operational life and required durability of the carrier member, etc.

In a typical arrangement, the distance that any signal is transmitted in the intracochlear section is relatively short, for example, in the order of 20 mm for the most apical electrode and only a few millimeters for the basally positioned electrodes. Thus, significantly thinner electrode elements 204, 206 will still have high enough conductivity to transmit the electrical signal without impacting on the efficiency of the stimulation.

In one embodiment, conductive pathways 206 are approximately 25 microns in diameter. In other embodiments, some or all conductive pathways 206 have a smaller diameter of 15-20 microns. In one particular embodiment, some or all conductive pathways 206 have a diameter of approximately 10 microns, and in one preferred embodiment, 5 microns in the intra-cochlea region. It should be appreciated that in alternative embodiments, not all conductive pathways 206 have the same dimensions and that some conductive pathways 206 have different dimensions along different portions of their length.

Thus, conductors 206 with a more substantial cross-section are typically utilized to survive mechanical challenges. Also, the length of certain conductors 206 in the extracochlear section is typically around 200 mm, an order of magnitude higher than the intracochlear section. So, thicker conductors are typically required to ensure that conductivity is high enough not to impact on the efficiency of electrical stimulation.

Figure 3:
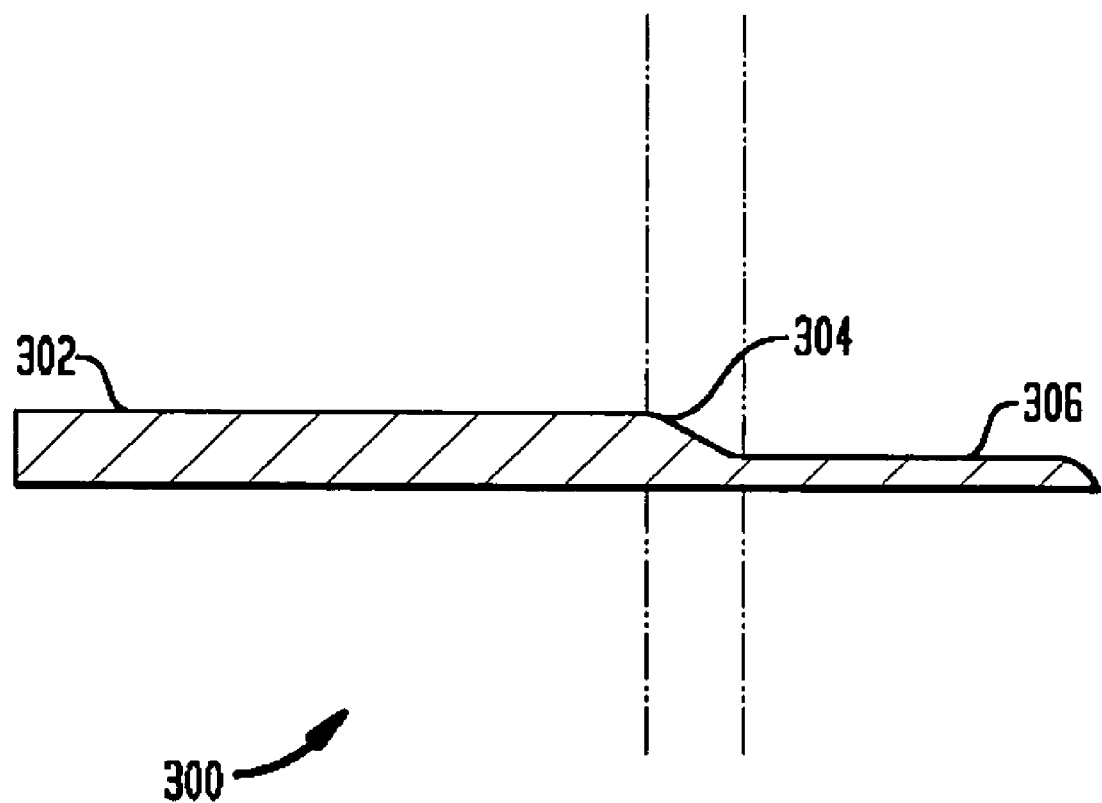
FIG. 3 is a cross-sectional view of a single conductive pathway of an electrode assembly according to one embodiment of the present invention.

FIG. 3 is a cross-sectional view of a single conductive pathway 206 of an electrode assembly according to one embodiment of the present invention, referred to herein as conductive pathway 300. Conductive pathway 300 has a first portion 302 of uniform first thickness, a second transition portion 304 that has a decreasing thickness, and a third portion 306 that is of a uniform second thickness which is less than the first thickness.

First portion 302 is arranged to be placed in the extracochlear region. Second transitional portion 302 is arranged to be placed near cochleostomy 142, but not outside the facial recess. The third portion 306 is arranged to be placed in the intracochlear region. Third portion 306 is closer to the distal end of the electrode the carrier member than the first and second portions 302, 304.

Figure 4A:
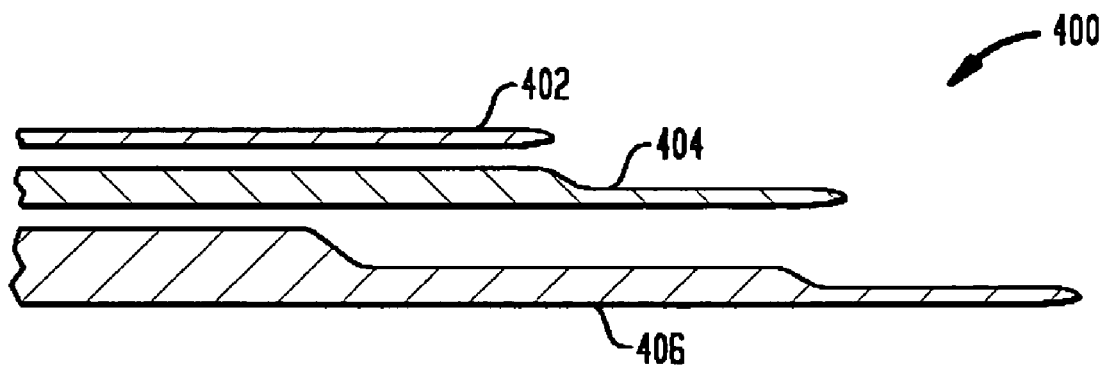
FIG. 4A is a cross-sectional view of a number of conductive pathways of an electrode assembly formed from a plurality of layers of worked platinum according to an embodiment of the present invention.
Figure 4B:
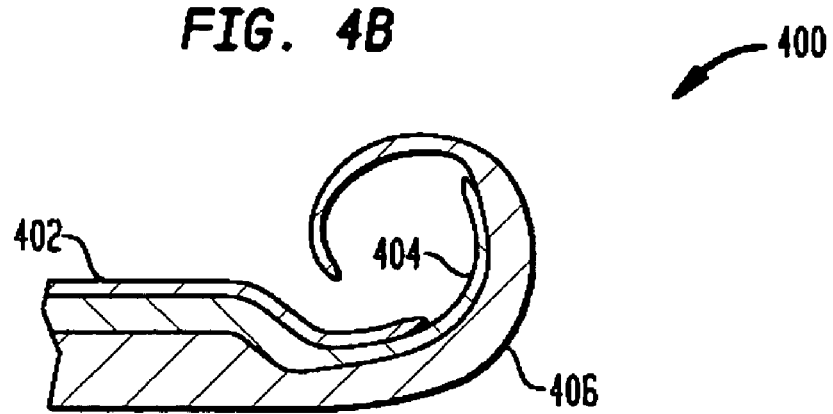
FIG. 4B is a cross-sectional view of the conductive pathways illustrated in FIG. 4A shown integrated in a curved configuration.

The general configuration shown in FIG. 3 may be used to build an electrode arrangement as described below with reference to FIGS. 4A and 4B. Electrode arrangement 400 comprises a series of electrodes 402, 404 and 406 and conductive pathways can be formed from two or more layered worked sheets of electrically conducting material, such as platinum. The conductive pathway or pathways formed from one of the sheets (for example, sheet 406) may have a different cross-sectional profile to the other signal pathways formed from the other sheet or sheets such as sheets 402 and 404.

In one example, the variation in the thickness of the conductive areas may be created by selective deposition. For example, conductive polymers may be deposited in predetermined patterns to create conductive portions (for example, electrodes and conductors). In another example, a combination of the two or more techniques may be used. A base conductive layer may be produced by, for example, EDM, featuring thickness in the range of a few millimeters or even less. Then, polymer can be selectively grown only in predetermined areas.

Figure 8:
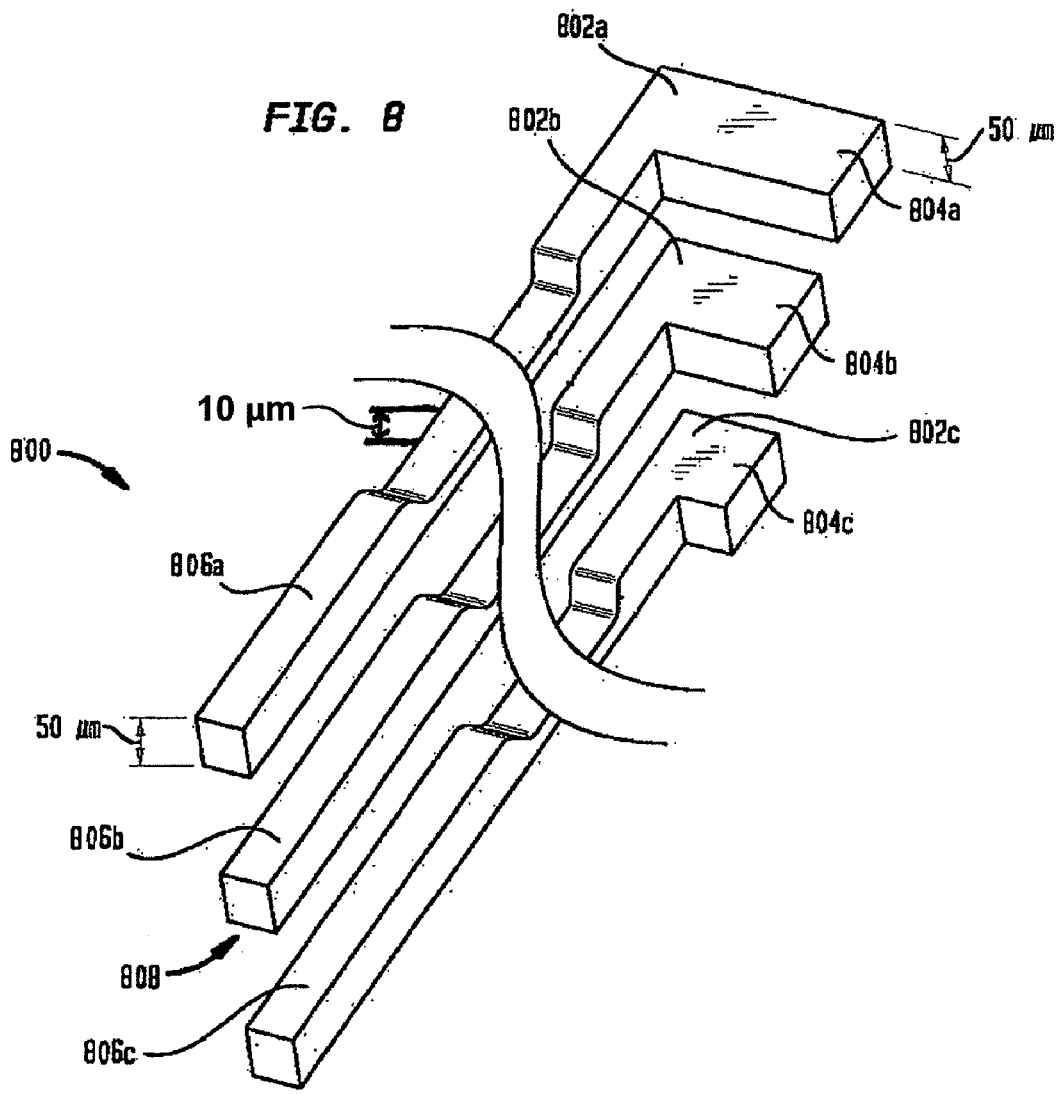
FIG. 8 is a perspective view of a number of conductive pathways of an electrode assembly according to another embodiment of the invention.

Referring now to FIG. 8, there is an electrode arrangement 800 of electrodes 802A, 802B and 802C. Each electrode 802A-802C comprises an electrode pad 804A, 804B and 804C, respectively, each connected to a respective conductive pathway 806A, 806B and 806C. Preferably, the thickness of each electrode pad 804 is around 50 μm, although this can be varied to between approximately 5 μm and approximately 100 μm.

Referring to the most distal electrode pad 804A, conductive pathway 806A extending from this pad starts to reduce in thickness at a place immediately adjacent to electrode pad 804b of neighboring electrode 802B. In this example, the region of reduced thickness is on the order of 10 μm. In particular, this arrangement of variable thickness helps to protect against breakage near electrode pad 804A. Similarly, conductive pathway 806B extending from electrode pad 806A starts to reduce in thickness at a place immediately adjacent, or just behind, the next adjacent electrode pad 804C.

An increase in the thickness of each conductive pathway can be made at the proximal regions, as indicated by reference numeral 808, where the pathway will be eventually situated in an extracochlear position.

The arrangement of FIG. 8 advantageously provides an intracochlear portion that is thin and flexible, with a smaller, gentle perimodiolar array. At the same time, the arrangement of FIG. 8 provides a relatively robust portion for implantation in the extracochlear portion, thus reducing the likelihood of damage due to constant mechanical movement.

Figure 5:
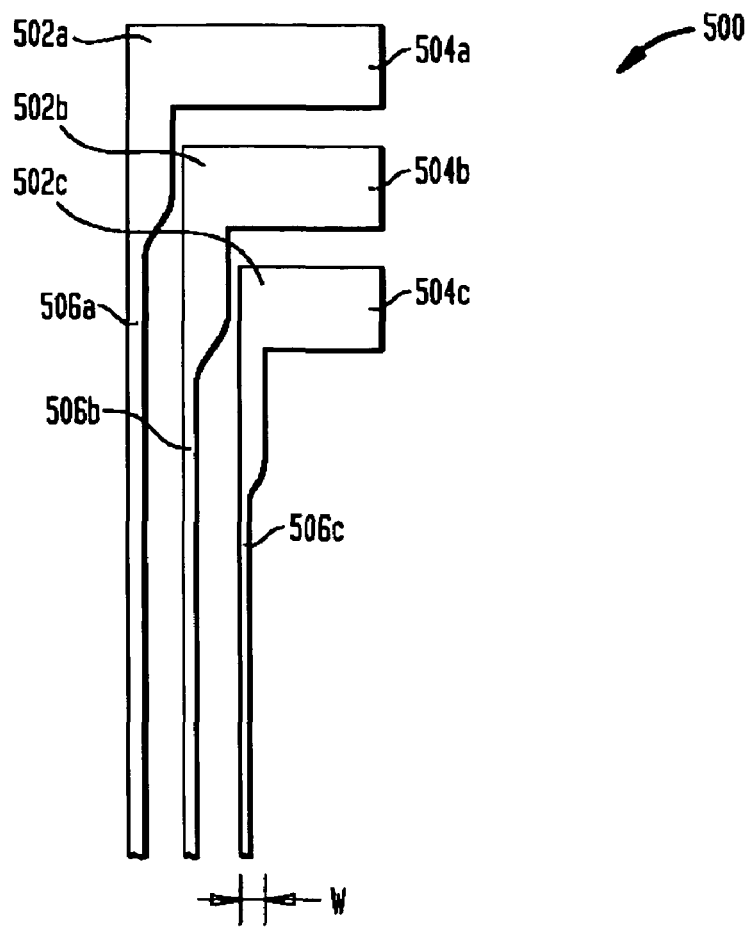
FIG. 5 is a plan view of a number of conductive pathways of an electrode assembly according to another embodiment of the present invention.

Referring to FIG. 5, a similar arrangement as FIG. 8 is shown, except that a reduction in dimension occurs in the width (w), rather than the thickness of the conductive pathway. It is noted that in other arrangements, one conductive pathway can be reduced in thickness, whereas the adjacent conductive pathway is reduced in width. Other such combinations are envisaged. In addition, FIG. 7C illustrates an electrode arrangement of electrodes 702a, 702b and 702c, each of which is respectively connected to a conductive pathway. Each of the conductive pathways has a first thickness at a first portion adjacent the electrode to which it is connected, and a second thickness smaller than the first thickness at a second portion more distant from the electrode.

Figure 7A:
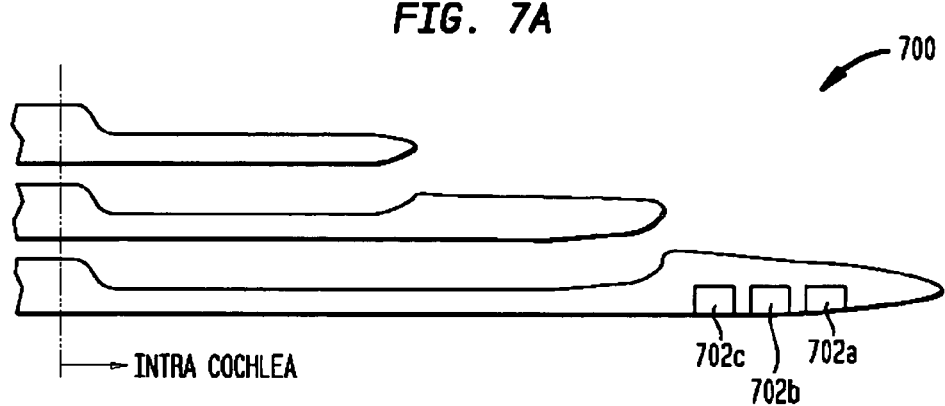
FIG. 7A is a cross-sectional view of a number of conductive pathways formed from a plurality of layers of worked platinum according to an embodiment of the present invention.
Figure 7B:
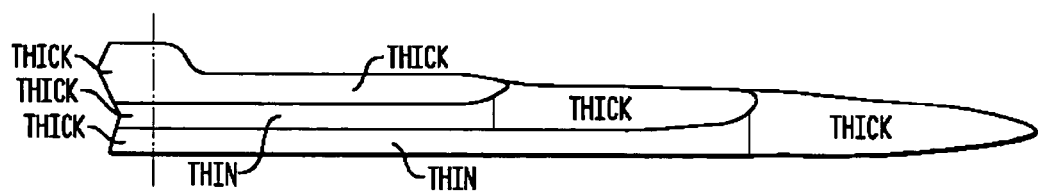
FIG. 7B is a cross-sectional view of a number of conductive pathways formed from a plurality of layers of worked platinum according to an embodiment of the present invention.
Figure 7C:
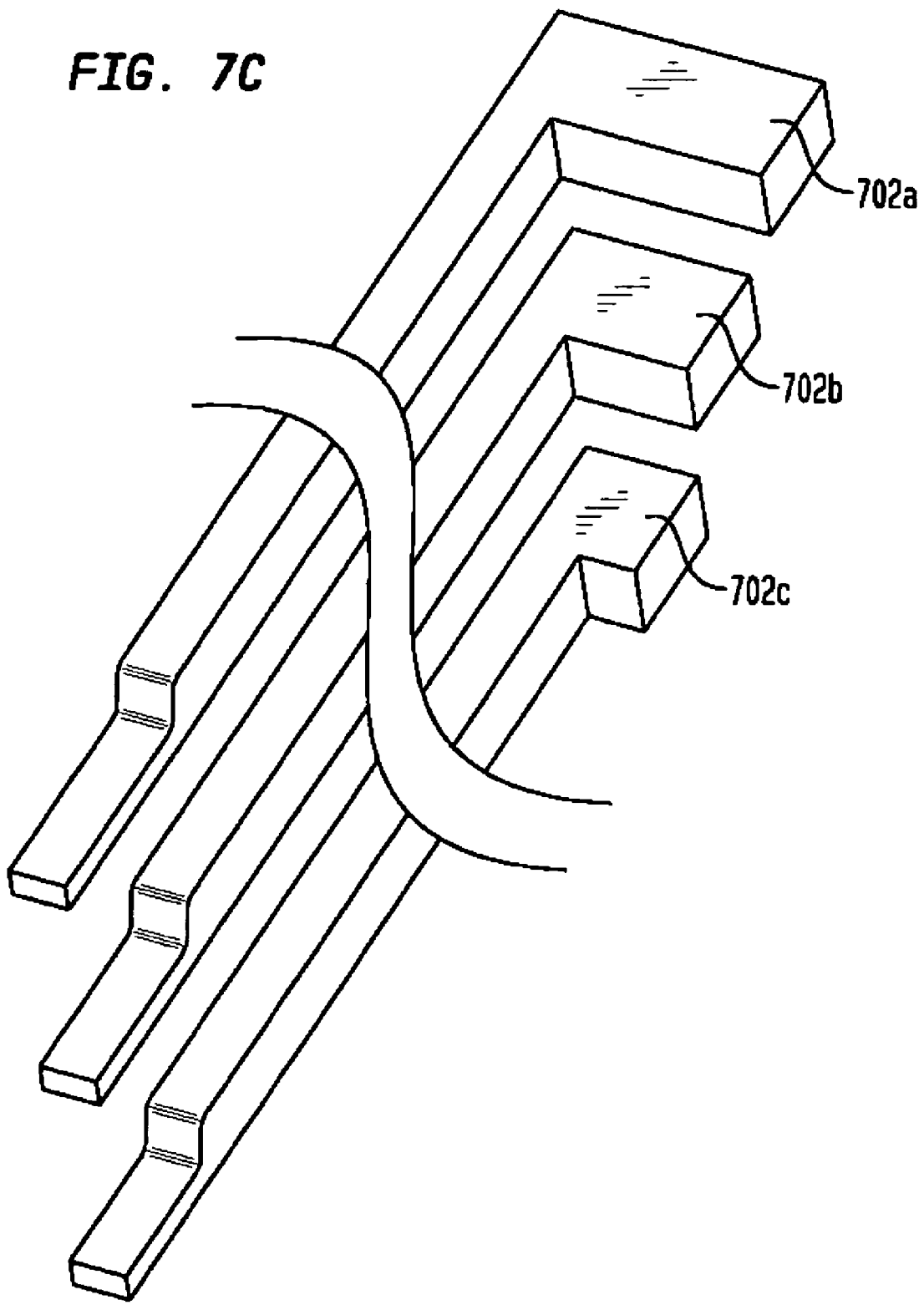
FIG. 7C is a perspective view of a number of conductive pathways of an electrode assembly according to another embodiment of the invention.

Turning now to FIGS. 7A and 7B, a layered method of manufacturing the electrode pad and conductive pathways of an electrode arrangement 700 is shown. Electrode arrangement includes electrodes 702a, 702b, and 702c. The principle of such layering is discussed in WO 02/089907.

Figure 6A:
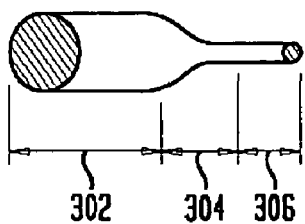
FIG. 6A is a perspective cross-sectional view of a portion of a conductive pathway in accordance with one embodiment of the present invention.
Figure 6B:
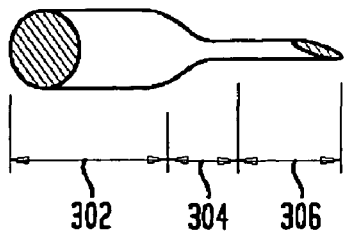
FIG. 6B is a perspective cross-sectional view of a portion of a conductive pathway in accordance with one embodiment of the present invention.

It will be appreciated by persons of ordinary skill in the art that numerous variations and/or modifications may be made to the invention, as shown in the specific embodiments, without departing from the spirit or scope of the invention. For example, the conductive pathways can be of generally round and/or elliptically shaped, as shown in FIGS. 6A and 6B, respectively.

Further, the present invention can be applied to other implantable medical devices including pacemakers, FES stimulators, recording devices such as neural activity sensors, implantable cables, and diagnostic devices.

As shown in the above embodiments, the portion of the signal pathways that have the reduced dimension (whether width, thickness, diameter, or combination thereof) are staggered or linearly offset from each other. This results in the quantity of signal pathways that have a larger dimension at any point along the length of the carrier member being less than the total quantity of signal pathways. For example, in FIG. 5, there is a point at which signal pathways 506A and 506B have a smaller width while signal pathway 506C has a larger width. In this embodiment the transition from the larger to smaller dimension on, for example, electrode 502A, occurs immediately adjacent to the electrode pad 504A of the adjacent electrode 504A. It should be appreciated that the portion of each signal pathway that has the reduced dimension need not be the same length for each electrode in an electrode assembly, nor do they have the same relative offset.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

The invention claimed is:

1. An implantable electrode assembly for a stimulating medical device comprising:
an elongate carrier member;
a plurality of electrodes disposed at least partially on or in said carrier member each configured to deliver to a recipient stimulating signals received from a stimulator unit; and
a plurality of signal pathways, each extending through at least a portion of said carrier member and configured to deliver one or more of the stimulation signals to a respective one of the electrodes, wherein, when said carrier member is in a substantially straight configuration, each of said signal pathways has a non-uniform cross-sectional profile over a substantially linear portion of said signal pathway.

2. The electrode assembly of claim 1, wherein each of said plurality of signal pathways decreases in one or more of thickness and width over a length of said carrier member.

3. The electrode assembly of claim 1, wherein the substantially linear portion of each of said signal pathways includes a first portion having a substantially uniform first thickness, a third portion having a substantially uniform third thickness that is less than said first thickness, and a second portion interposed between said first and third portions and having a second thickness that decreases from said first thickness to said third thickness.

4. The electrode assembly of claim 3, wherein said carrier member has a proximal end and a distal end, and wherein said third portion is closer to said distal end than are said first and second portions.

5. The electrode assembly of claim 4, wherein said first, second and third thicknesses are each a diameter of the signal pathway.

6. The electrode assembly of claim 1, wherein each of said plurality of signal pathways is formed from a worked sheet of electrically-conductive material.

7. The electrode assembly of claim 6, wherein each of said plurality of electrodes is formed from said worked sheet.

8. The electrode assembly of claim 6, wherein said worked sheet of electrically conductive material is formed of platinum.

9. The electrode assembly of claim 8, wherein said worked sheet of electrically conductive material has a maximum thickness of approximately 50 microns.

10. The electrode assembly of claim 1,
wherein each of said plurality of signal pathways is electrically insulated from other of said plurality of signal pathways that are immediately adjacent said each signal pathway.

11. The electrode assembly of claim 10, wherein each of said plurality of signal pathways has a width of between approximately 1 and approximately 100 microns.

12. The electrode assembly of claim 10, wherein the spacing between neighboring signal pathways is between about 1 and 100 microns.

13. The electrode assembly of claim 1, wherein said signal pathways are disposed for at least a portion of their lengths in a parallel arrangement.

14. The electrode assembly of claim 1, wherein at least one of said plurality of signal pathways is comprised of a first planar portion and at least a second planar portion, the second planar portion being oriented at an angle to the first planar portion.

15. The electrode assembly of claim 14, wherein said second planar portion is oriented at an angle of approximately 90 degrees to said first planar portion.

16. The electrode assembly of claim 14, wherein said first and second planar portions are joined by a joining portion.

17. The electrode assembly of claim 14, wherein said at least one signal pathway comprises a plurality of first and second planar portions.

18. The electrode assembly of claim 1, wherein said carrier member is formed from a silicone.

19. The electrode assembly of claim 1, wherein said stimulating medical device is a cochlear implant.

20. The electrode assembly of claim 1, wherein each of said plurality of signal pathways includes first, second and third portions, wherein the second portion is disposed between the first and third portions and one or more of a width and a thickness of the signal pathway is greater in each of the first and third portions than in the second portion.

21. The electrode assembly of claim 20, wherein said carrier member has proximal and distal ends, the first portion is disposed nearer the distal end than the second portion and the third portion is disposed nearer the proximal end than the second portion.

22. A prosthetic hearing device comprising:
a stimulator unit;
an implantable electrode assembly for a stimulating medical device comprising:
an elongate carrier member;

a plurality of electrodes disposed at least partially on or in said carrier member each configured to deliver to a recipient stimulating signals received from said stimulator unit; and a plurality of signal pathways, each extending through at least a portion of said carrier member and configured to deliver one or more of the stimulation signals to a respective one of the electrodes, wherein, when said carrier member is in a substantially straight configuration, each of said signal pathways has a non-uniform cross-sectional profile over a substantially linear portion of said signal pathway.

23. The prosthetic hearing device of claim 22, wherein each of said plurality of signal pathways decreases in one or more of thickness and width over a length of said carrier member.

24. The prosthetic hearing device of claim 22, wherein the substantially linear portion of each of said signal pathways includes a first portion having a substantially uniform first thickness, a third portion having a substantially uniform third thickness that is less than said first thickness, and a second portion interposed between said first and third portions and having a second thickness that decreases from said first thickness to said third thickness.

25. The prosthetic hearing device of claim 24, wherein said carrier member has a proximal end and a distal end, and wherein said third portion is closer to said distal end than are said first and second portions.

26. The prosthetic hearing device of claim 22, wherein each of said plurality of signal pathways is formed from a worked sheet of electrically-conductive material.

27. The prosthetic hearing device of claim 26, wherein each of said plurality of electrodes is formed from said worked sheet.

28. The prosthetic hearing device of claim 26, wherein said worked sheet of electrically-conductive material is formed of platinum.

29. The prosthetic hearing device of claim 28, wherein said worked sheet of electrically-conductive material has a maximum thickness of approximately 50 microns.

30. The prosthetic hearing device of claim 22,
wherein each of said plurality of signal pathways is electrically insulated from other of said plurality of signal pathways that are immediately adjacent said each signal pathway.

31. The prosthetic hearing device of claim 30, wherein each of said plurality of signal pathways has a width of between approximately 1 and approximately 100 microns.

32. The prosthetic hearing device of claim 30, wherein the spacing between neighboring signal pathways is between about 1 and 100 microns.

33. The prosthetic hearing device of claim 22, wherein said signal pathways are disposed for at least a portion of their lengths in a parallel arrangement.

34. The prosthetic hearing device of claim 22, wherein at least one of said plurality of signal pathways is comprised of a first planar portion and at least a second planar portion, the second planar portion being oriented at an angle to the first planar portion.

35. The prosthetic hearing device of claim 34, wherein said second planar portion is oriented at an angle of approximately 90 degrees to said first planar portion.

36. The prosthetic hearing device of claim 34, wherein said first and second planar portions are joined by a joining portion.

37. The prosthetic hearing device of claim 34, wherein said at least one signal pathway comprises a plurality of first and second planar portions.

38. The prosthetic hearing device of claim 22, wherein said carrier member is formed from a silicone.

39. The prosthetic hearing device of claim 22, wherein said prosthetic hearing device is a cochlear implant.

40. The prosthetic hearing device of claim 22, wherein each of said plurality of signal pathways includes first, second and third portions, wherein the second portion is disposed between the first and third portions and one or more of a width and a thickness of the signal pathway is greater in each of the first and third portions than in the second portion.

41. The prosthetic hearing device of claim 40, wherein said carrier member has proximal and distal ends, the first portion is disposed nearer the distal end than the second portion and the third portion is disposed nearer the proximal end than the second portion.

42. The prosthetic hearing device of claim 25, wherein said first, second and third thicknesses are each a diameter of the signal pathway.

* * * * *